(12) United States Patent
Schobben et al.

(10) Patent No.: US 12,109,408 B2
(45) Date of Patent: Oct. 8, 2024

(54) IMPLANTABLE ELECTRICAL STIMULATION DEVICE WITH A FLEXIBLE ELECTRODE

(71) Applicant: SALVIA BIOELECTRONICS B.V., Eindhoven (NL)

(72) Inventors: Daniël Schobben, Eindhoven (NL); Hubert Martens, Eindhoven (NL); Mailys Guillard, Eindhoven (NL)

(73) Assignee: SALVIA BIOELECTRONIC B.V., Eindhoven (NL)

( * ) Notice: Subject to any disclaimer, the term of this patent is extended or adjusted under 35 U.S.C. 154(b) by 347 days.

(21) Appl. No.: 17/609,755

(22) PCT Filed: May 8, 2020

(86) PCT No.: PCT/IB2020/054387
§ 371 (c)(1),
(2) Date: Nov. 8, 2021

(87) PCT Pub. No.: WO2020/225793
PCT Pub. Date: Nov. 12, 2020

(65) Prior Publication Data
US 2022/0218985 A1    Jul. 14, 2022

(30) Foreign Application Priority Data
May 9, 2019   (NL) .................................. 2023093

(51) Int. Cl.
*A61N 1/05*    (2006.01)
*A61N 1/36*    (2006.01)

(52) U.S. Cl.
CPC ......... *A61N 1/0534* (2013.01); *A61N 1/0531* (2013.01); *A61N 1/0551* (2013.01);
(Continued)

(58) Field of Classification Search
CPC ....................................................... A61N 1/05
See application file for complete search history.

(56) References Cited

U.S. PATENT DOCUMENTS

| 6,236,892 B1 | 5/2001 | Feler |
| 7,363,082 B2 * | 4/2008 | Ransbury ........... A61N 1/37512 607/116 |

(Continued)

OTHER PUBLICATIONS

Search Report for International Patent Application PCT/IB2020/054387, mailed on Aug. 28, 2020.
(Continued)

*Primary Examiner* — Tammie K Marlen
(74) *Attorney, Agent, or Firm* — Fresh IP PLC; Clifford D. Hyra; Aubrey Y. Chen

(57) ABSTRACT

A mismatch in curvature of an electrode lead section may create unexpected and/or unpredictable electrical resistance with underlying tissue. In addition, repeated movement of the relevant areas of the body may even worsen the mismatch. Implants for electrical stimulation require low electrical resistance conductors for stimulation electrodes, return electrodes and interconnections which conventionally use metal for wires and contacts. These conductors reduce the flexibility, and the problem becomes worse as the number of electrodes increases.

An implantable stimulation device is provided with an elongated substrate, one or more interconnections, a flexible electrode with two portions, separated by one or more bending interruptions, wherein the first portion and second portion are in direct electrical connection through the one or more interconnections.

The electrode portions on opposite sides of the bending points are electrically connected allowing the mechanical bending and the electrical connections to be optimized separately.

22 Claims, 9 Drawing Sheets

(52) U.S. Cl.
CPC ..... *A61N 1/36007* (2013.01); *A61N 1/36064* (2013.01); *A61N 1/36075* (2013.01); *A61N 1/36085* (2013.01); *A61N 1/361* (2013.01); *A61N 1/36117* (2013.01)

(56) References Cited

U.S. PATENT DOCUMENTS

| | | |
|---|---|---|
| 8,260,434 B2 | 9/2012 | Digiore et al. |
| 9,216,282 B1 | 12/2015 | Moffitt |
| 9,814,889 B2 * | 11/2017 | Strommer ............. A61M 25/09 |
| 10,188,853 B2 | 1/2019 | Agrawal |
| 11,278,724 B2 * | 3/2022 | Law ................... A61N 1/0456 |
| 2005/0203602 A1 | 9/2005 | Wallace |
| 2008/0221653 A1 * | 9/2008 | Agrawal ............ A61N 1/36046 |
| | | 607/118 |
| 2010/0070010 A1 | 3/2010 | Simpson |
| 2015/0099959 A1 | 4/2015 | Bonmassar |
| 2018/0008824 A1 | 1/2018 | Gonzalez |
| 2018/0122824 A1 | 7/2018 | Gupta |

OTHER PUBLICATIONS

Non-Final Office Action dated Jan. 16, 2024, issued in JP Patent Application No. 2021-566579; 7 pages.
Non-Final Office Action dated Jul. 28, 2023, issued in IN Patent Application No. 202127052049; 6 pages.

* cited by examiner

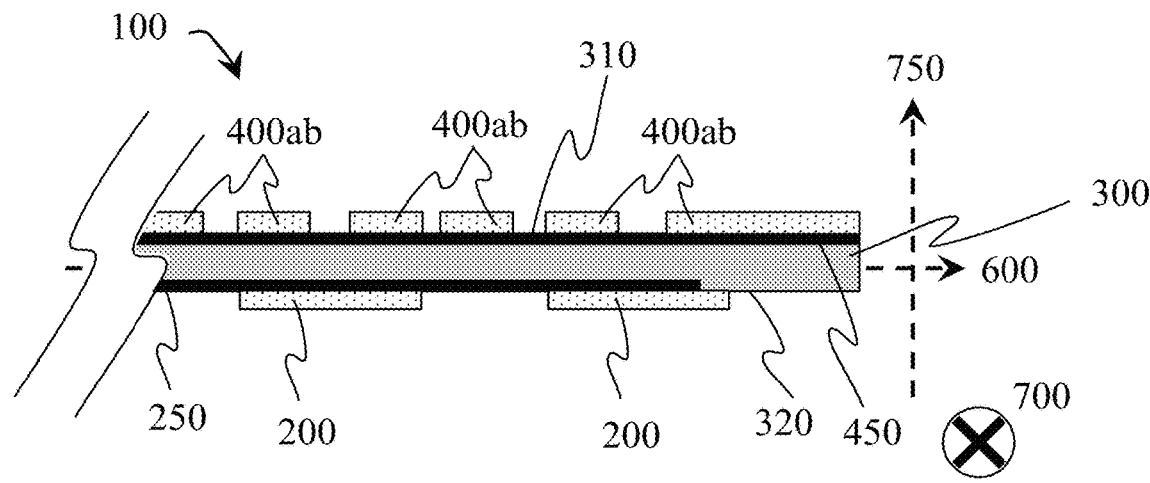
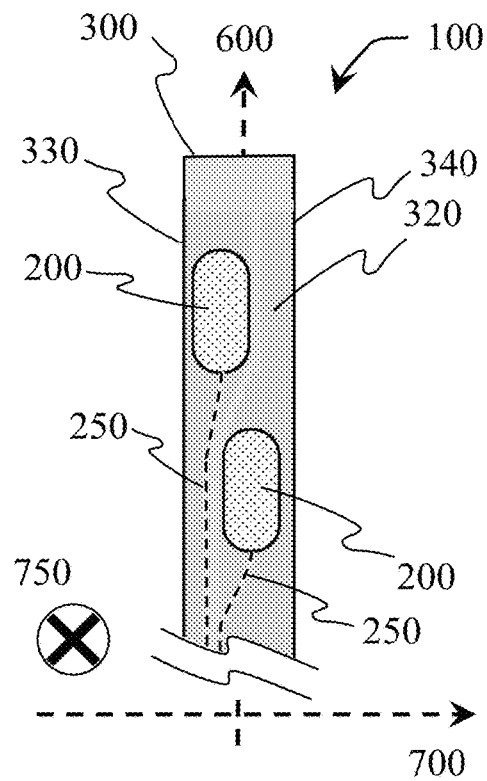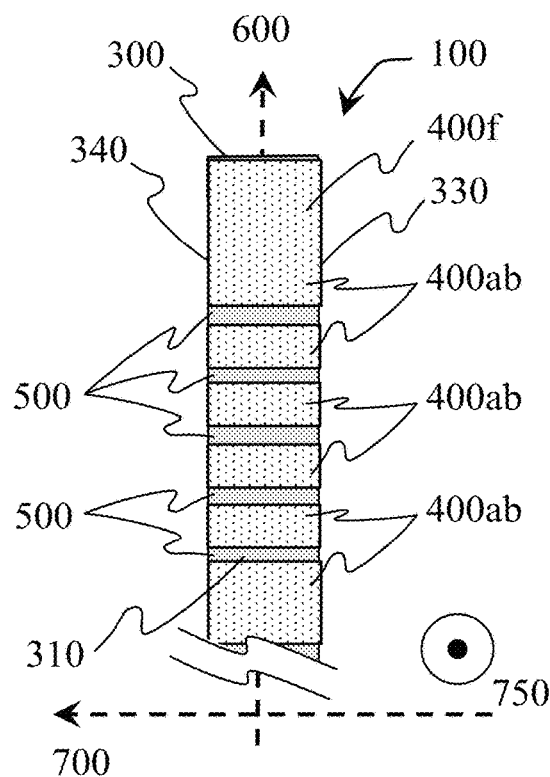
Fig. 1A
Fig. 1B    Fig. 1C

IMPLANTABLE ELECTRICAL STIMULATION DEVICE WITH A FLEXIBLE ELECTRODE

FIELD

The present disclosure relates to an implantable stimulation device for providing electrical stimulation comprising a flexible electrode. It also relates to a stimulation system comprising such an implantable stimulation device.

BACKGROUND

Implantable electrical stimulation systems may be used to deliver electrical stimulation therapy to patients to treat a variety of symptoms or conditions such as headaches, lower back pain and incontinence.

In many electrical stimulation applications, it is desirable for a stimulation device, typically comprising a therapeutic lead (a lead comprises electrodes and electrical connections), to provide electrical stimulation to one or more precise locations within a body in many cases, precisely aligning of the stimulation electrodes during implantation may be difficult due to the curvature of tissues and anatomical structures. A mismatch in curvature of the electrode section of a lead may create unexpected and/or unpredictable electrical resistance between one or more electrode and the underlying tissue. In addition, repeated movement of the relevant areas of the body may even worsen the mismatch. A particular problem with subcutaneous implants is that even small differences in flexibility between the implant and surrounding tissue may affect patient comfort, and can cause irritation of the overlying skin.

More recently, use has been made of polymers, which have an inherent flexibility. However, implants for electrical stimulation require low resistance conductors for stimulation electrodes, return electrodes and interconnections which conventionally use metal for wires and contacts. These conductors reduce the flexibility, and the problem becomes worse as the size of electrodes increases due to a desire to offer a higher degree of customization, to provide more functionality or to lower the electrical resistance.

US application US 2015/099959 describes an implantable electrode array including an organic substrate material configured to be implanted into an in vivo environment and to optionally dissolve and be absorbed, and an electrode mounted to the organic substrate material and configured to acquire signals generated by the in vivo environment. The electrode array includes a connection pad mounted to the organic substrate, and an MRI-compatible conductive trace formed between the electrode and the connection pad.

PCT application WO 2018/122824 describes a cortical stimulating and recording electrode comprising a flexible support element for at least one conductive element, with a head end and a tail end. The conductive element has at least one head contact and at least one tail contact, arranged at the head end and tail end respectively of the flexible support element, such that said conductive element transmits signals from said head contact to said tail contact and vice versa. Moreover the conductive element is composed of a conductive track formed of a layer of conductive ink deposited on said flexible support element.

US application US 2018/0008821 describes thin film devices and methods of manufacturing and implanting the same. In one implementation, a shaped insulator is formed having an inner surface, an outer surface, and a profile shaped according to a selected dielectric use. A layer of conductive traces is fabricated on the inner surface of the shaped insulator using biocompatible metallization. An insulating layer is applied over the layer of conductive traces. An electrode array and a connection array are fabricated on the outer surface of the shaped insulator and/or the insulating layer, and the electrode array and the connection array are in electrical communication with the layer of conductive traces to form a flexible circuit. The implantable thin film device is formed from the flexible circuit according to the selected dialectic use.

It is an object of the invention to provide an improved implantable stimulation device with a plurality of conductors that provides a higher degree of conformity with surrounding tissues and anatomical structures.

General Statements

According to a first aspect of the present disclosure, there is provided an implantable stimulation device comprising: an elongated substrate, disposed along a longitudinal axis, the substrate having a first and second surface disposed along substantially parallel transverse planes, the substrate further comprising: a flexible electrode, comprised in the first or second surface, and configured, in use, to be in contact with human or animal tissue; and one or more interconnections, disposed between the first and second surface; the flexible electrode further comprising: a first portion, disposed along a first portion plane, and a second portion, disposed along a second portion plane, the first portion and second portion being in direct electrical connection through the one or more interconnections and being separated by one or more bending interruptions, wherein one or more bending interruptions are configured and arranged to have a lower bending resistance than the first and second portion whereby an orientation of the first portion plane is allowed to deviate from an orientation of the second portion plane at the one or more bending interruptions; wherein the first portion and second portion are in direct electrical connection through the one or more interconnections.

A highly-configurable flexible electrode is provided by disposing it on a surface of an elongated substrate and including one or more bending interruptions. In addition, the portions on opposite sides of the bending points are electrically connected by low resistance interconnections, which allows the mechanical bending and the electrical connections to be optimized separately. One or more bending interruptions allows at least the electrode portion of an implantable device to conform to neighboring anatomical and tissue structures. This may also increase the tissue contact area of the flexible electrode. The presence of one or more interconnections allows the bending characteristics to be optimized without substantially affecting the electrical characteristics of the flexible electrode. The flexible electrode may be configured and arranged as a return electrode or stimulation electrode. A plurality of flexible electrodes may be provided.

Additionally or alternatively, the conformable shape of the flexible electrode in cross-section comprises one or more bending interruptions separating two portions having a higher rigidity than the bending interruptions.

According to a further aspect of the present disclosure, there is provided an implantable stimulation device, wherein the flexible electrode has a longitudinal extent along the longitudinal axis; and the one or more bending interruptions being configured and arranged to allow a deviation around a longitudinal axis. Alternatively or additionally, the flexible electrode has a transverse extent along a first transverse axis, the transverse axis being substantially perpendicular to the longitudinal axis; the one or more bending interruptions being configured and arranged to allow a deviation around a transverse axis.

Bending around a longitudinal axis and/or transverse axis allows a highly configurable implantable substrate. This means that substrate sections with electrodes (leads) that closely confirm to a high degree to surrounding tissue. It also allows very accurately shapeable substrate sections to be produced for specific anatomical dispositions, and even personalized shaping for highly-variable anatomical dispositions.

According to another aspect of the present disclosure, there is provided an implantable stimulation device wherein the tissue contact surface of the first portion is disposed along the first portion plane, and the tissue contact surface of the second portion is disposed along the second portion plane.

If a substrate section is made highly configurable, a high degree of tissue contact surface may be provided, up to the total surface area of the flexible electrode portions. This means that the actual tissue stimulation area of the one or more electrodes may be more predictable.

According to a still further aspect of the present disclosure, the flexible electrode further comprises one or more contiguous portions proximate the one or more bending interruptions, configured and arranged to increase or to maintain the bending resistance between the first and second portions. This may be described as a deformable electrode, allowing it to be bent into desired shapes and profiles which may be wholly or partially retained.

This allows the conductive properties between the electrode portions and the bending resistance to be separately optimized. Configuring and arranging the contiguous portion to increase or to maintain the bending resistance at the bending axes (for example, making the contiguous portion thinner and/or narrower), may be performed without substantially effecting the conductivity and without substantially affecting the operation of the flexible electrode. When suitably configured, it also allows a substrate section to retain a bending profile this may be advantageous when a healthcare professional is preparing the substrate section for implantation.

According to yet another aspect of the present disclosure, the one or more bending interruptions comprise one or more openings.

Openings may be advantageous because they are relatively straightforward to create using lithographic and etching techniques, and they also may provide a visual clue to a healthcare professional who is implanting the substrate section where the bending axes are disposed.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein:

FIGS. 1A, 1B and 1C depicts a first example of an implantable distal end of a stimulation device;

DETAILED DESCRIPTION

Figure 2A:
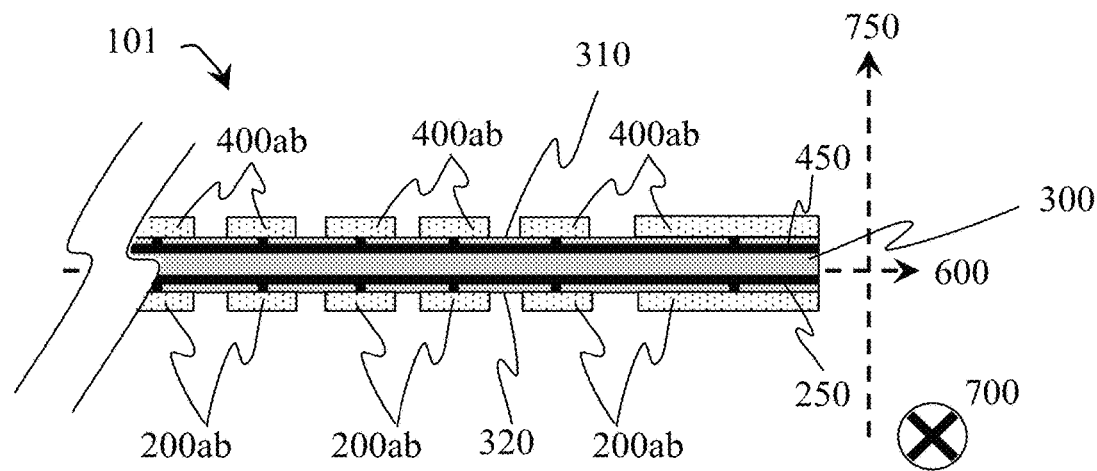
FIGS. 2A, 2B and 2C depicts a second example of an implantable distal end of a stimulation device.

In the following detailed description, numerous non-limiting specific details are given to assist in understanding this disclosure.

FIGS. 1A, 1B & 1C depict longitudinal cross-sections through a first embodiment 100 of an implantable distal end of a stimulation device comprising:

an elongated substrate 300, disposed along a longitudinal axis 600, the substrate having a first 310 and second 320 surface disposed along substantially parallel transverse planes 600, 700. For substrates 300 with a degree of flexibility, the degree to which the first 310 and second 320 surface are along substantially parallel transverse planes 600, 700 may be determined by laying the substrate 300 on a substantially flat surface. As depicted, the first surface 310 lies in a plane comprising the longitudinal axis 600 and a first transverse axis 700—the first transverse axis 700 is substantially perpendicular to the longitudinal axis 600. As depicted, the plane of the first surface 310 is substantially perpendicular to the plane of the cross-section drawing (substantially perpendicular to the surface of the paper). The substrate 300 has a thickness or extent along a second transverse axis 750 this second transverse axis 750 is substantially perpendicular to both the longitudinal axis 600 and the first transverse axis 700 it lies in the plane of the drawing (along the surface of the paper) as depicted. The first surface 310 is depicted as an upper surface and the second surface 320 is depicted as a lower surface.

To clarify the different views, the axes are given nominal directions:

the longitudinal axis 600 extends from the proximal end (not depicted) on the left, to the distal end, depicted on the right of the page;

the first transverse axis 700 extends into the page as depicted; and the second transverse axis 750 extends from bottom to top as depicted.

For example, the elongated substrate 300 may comprise an elastomeric distal end composed of silicone rubber, or another biocompatible, durable polymer such as siloxane polymers, polydimethylsiloxanes, polyurethane, polyether urethane, polyetherurethane urea, polyesterurethane, polyamide, polycarbonate, polyester, polypropylene, polyethylene, polystyrene, polyvinyl chloride, polytetrafluoroethylene, polysulfone, cellulose acetate, polymethylmethacrylate, polyethylene, and polyvinylacetate. Suitable examples of polymers, including LCP Liquid Crystal Polymer), are described in "Polymers for Neural Implants", Hassler, Boretius, Stieglitz, Journal of Polymer Science: Part B Polymer Physics, 2011, 49, 18-33 (DOI 10.1002/polb.22169), In particular, Table 1 is included here as reference, depicting the properties of Polyimide (UBE U-Varnish-S), Parylene C (PCS Parylene C), PDMS (NuSil MED-1000), SU-8 (Micro-Chem SU-8 2000 & 3000 Series), and LCP (Vectra MT1300).

Flexible substrates 300 are also preferred as they follow the contours of the underlying anatomical features very closely. Very thin substrates 300 have the additional advantage that they have increased flexibility.

Preferably, the flexible substrate 300 comprises an LCP, Parylene and/or a Polyimide. LCPs are chemically and biologically stable thermoplastic polymers which allow for hermetic sensor modules having a small size and low moisture penetration.

Advantageously, an LCP may be thermoformed allowing complex shapes to be provided. Very thin and very flat sections of an LCP may be provided. For fine tuning of shapes, a suitable laser may also be used for cutting. For example, LCP substrates 300 with thicknesses (extent along the second transverse axis 750) in the range 50 microns (um) to 720 microns (um) may be used, preferably 100 microns (um) to 300 microns (um). For example, values of 150 um (micron), 100 um, 50 um, or 25 um may be provided. Similarly, substrate widths (extent along the first transverse axis 700) of 2 mm to 20 mm may be provided using LCP, for example.

At room temperature, thin LCP films have mechanical properties similar to steel. This is important as implantable substrates 300 must be strong enough to be implanted, strong enough to be removed (explanted) and strong enough to follow any movement of the neighboring anatomical features and/or structures.

LCP belongs to the polymer materials with the lowest permeability for gases and water. LCPs can be bonded to themselves, allowing multilayer constructions with a homogenous structure.

In contrast to LCPs, polyimides are thermoset polymers, which require adhesives for the construction of multilayer substrates. Polyimides are a thermoset polymer material with high temperature and flexural endurance.

An LCP may be used, for example, to provide a substrate having multilayers (not depicted) in other words, several layers of 25 um (micron) thickness. Electrical interconnections and/or interconnect layers may also be provided by metallization using techniques from the PCB (Printed Circuit Board) industry, such as metallization with a biocompatible metal such as gold or platinum. Electro-plating may be used. These electrical interconnections and/or interconnect layers may be used to provide electrical energy to any electrodes.

Preferably, a low aspect ratio is used for the elongated substrate to reduce the chance of implantation problems for example a ratio of width (extent along the first transverse axis 700) to height (thickness or extent along the second transverse axis 750) of less than 10, such as 0.3 mm high and 10 mm wide.

The device 101 of FIG. 1 further comprises:
  a flexible electrode 400, comprised in the first surface 310, and configured, in use, to be in contact with human or animal tissue. The flexible electrode 400 comprises two or more portions 400a, 400b (400ab), separated by one or more bending interruptions 500. It is configured as a return electrode 400.

"Comprised in" the first or second surface means that flexible electrode 400 is relatively thin, and attached to the first 310 or second 320 surface. The electrode 400 may also be embedded in the first 310 or second 320 surface.

The first portion 400a and second portion 400b are disposed on opposing sides of the one or more interruptions 500. In some cases, they may oppose each other, as depicted in FIG. 1. In terms of this disclosure, there is no substantial functional difference between "a" and "b" portions—they may be interchanged. Conductor material disposed between two or more bending interruptions 500 may comprise one or more "a" portions and one or more "b" portions.

The portions 400ab are considered to be comprised in the same electrode (portions of the same electrode), because they are in direct electrical connection—in other words, they are connected such that the stimulation energy applied by a stimulation system (not depicted) is substantially the same at substantially the same time instance (usually measured as a voltage, a current, a power or any combination thereof) in each portion 400ab of the flexible return electrode 400.

This is not the same as two adjacent electrodes. Adjacent electrodes are configured and arranged to provide substantially different energies at substantially the same time, and/or substantially the same energy at substantially different times. In the context of this disclosure, electrodes that have separate electrical connections to an electrical energy source are considered "adjacent" they are not considered portions of the same electrode.

The device 101 of FIG. 1 further comprises:
  one or more bending interruptions 500 between two portions 400ab of the flexible electrode 400, configured and arranged to allow the flexible return electrode 400 to deform by bending at the disposition of the one or more bending interruptions 500. In other words, if a first portion 400a is disposed along a first portion plane and a second portion 400b is disposed along a second portion plane, the one or more bending interruptions 500 between these two portions 400ab is configured and arranged to deviate from an orientation of the second portion plane at the one or more bending interruptions 500.

The device 101 of FIG. 1 further comprises:
  one or more interconnections 450, configured and arranged to directly electrically connect two or more portions 400ab. Additionally, the one or more interconnections 450 may be configured to provide the flexible return electrode 400 with electrical energy from a stimulation system (not depicted). The one or more interconnections 450 are disposed between the first 310 and second surface 320. They may comprise one or more conductors, such as a metal, formed as required for example, in one or more conductive: wire, strand, foil, lamina, plate, and/or sheet. They may be a substantially contiguous (one conductor). They may also comprise more than one conductor, configured and arranged to be, in use, electrically connected with each other proximate the corresponding bending interruption 500 in other words, the one or more conductors are configured and arranged to be substantially electrically contiguous in use.

An interconnection 450 in the context of this disclosure is not configured or arranged to be, in use, in contact with human or animal tissue. For example, by embedding the one or more interconnections 450 in a low conductance or insulating substrate 300, such as LCP. Note that an interconnection 450 may be comprised in the first 310 or second surface 320 if it is configured and arranged to be low conductance and/or insulating by including one or more layers between the interconnection 450 and any human or animal tissue.

"Comprised in" the first 310 or second 320 surface means that the interconnection 450 is relatively thin, and attached to the first 310 or second 320 surface. The interconnection 450 may also be embedded in the first 310 or second 320 surface.

Additionally or alternatively, the substrate 300 may be a multilayer, comprising one or more electrical interconnections and/or electrical interconnect layers 450. If an LCP multilayer is used, the thickness (extent of the substrate 300 along the second transverse axis 750 or the perpendicular distance between the first surface 310 and the second surface 320) may be typically approximately 150 um (micron) in the sections with no electrode portions 400*ab* or interconnections 450, 250 um in the sections with an electrode 220, and 180 um in the sections with an electrical interconnection 250. If multilayers are used, one or more electrical interconnection layers of 25 um (micron) thickness may be used, for example.

Alternatively, the flexible return electrode 400 may also be comprised in the second surface 320. The device may comprise a plurality of flexible return electrodes 400 comprised in the first 310 and/or second 320 surface.

In this example, the flexible electrode 400 is configured as a return electrode it is configured to provide, in use, an electrical return for one or more stimulation electrode 220. In other words, the electrical return 400 closes the electrical circuit. It may also be similarly configured to provide an electrical ground for a correspond electrical energy source.

The device 101 of FIG. 1 further comprises:
one or more stimulation electrodes 200, comprised in the second surface 320 and configured to transmit energy, in use, to human or animal tissue (after implantation).
one or more electrical interconnections 250, configured to provide the one or more stimulation electrodes 200 with electrical energy from a stimulation system (not depicted). The flexible electrode 400 is configured to provide, in use, an electrical return for these one or more stimulation electrode 220.

"Comprised in the second surface" means that the one or more stimulation electrode 200 is relatively thin, and attached to the second surface 320. The electrode 200 may also be embedded in the second surface 320.

Additionally or alternatively, the device may comprise one or more stimulation electrodes 200, comprised in the first surface 310.

In general, one or more stimulation electrodes 200 may be provided. The number, dimensions and/or spacings of the stimulating electrodes 200 may be selected and optimized depending on the treatment for example, if more than one electrode 200 is provided, each electrode 200 may provide a separate stimulation effect, a similar stimulation effect or a selection may be made of one or two electrodes 200 proximate the tissues where the effect is to be created. Two or more stimulation electrodes 200 may be made active if stimulation over a larger area is required and/or at a disposition between the active electrodes 200. The electrodes 200 may comprise a conductive material such as gold, silver, platinum, iridium, and/or platinum/iridium alloys and/or oxides. An implantable device with a distal end (or lead) suitable for implant may comprise, for example, 12 stimulation electrodes over a length of 15 cm. A stimulation electrode may have dimensions on the order of 6 to 8 mm along the longitudinal axis 600 and 3 to 5 mm along the first transverse axis 700, so approximately 18 to 40 square mm (mm$^2$). If a strip of 4 mm wide (extent along the first transverse axis 700) is provided as a return electrode, then a length (extent along the longitudinal axis 600) 4.5 to 10 mm also provides a contact area of 18 to 40 square mm (mm$^2$). The electric field is more concentrated between the strip and the corresponding stimulation electrode.

FIG. 1B depicts a view of the second surface 320 of the implantable end of the stimulation device 100 depicted in FIG. 1A. In other words, the second surface 320 is depicted in the plane of the paper, lying along the longitudinal axis 600 (depicted from bottom to top) and in the first transverse axis 700 (depicted from left to right). The second transverse axis 750 extends into the page. This is the view facing the animal or human tissue which is stimulated (in use). The first surface 310 is not depicted in FIG. 1B, but lies at a higher position along the second transverse axis 750 (into the page), and is also substantially parallel to the plane of the drawing.

The one or more interconnections 250 are disposed between the second 320 surface and the first 310 surface, as depicted in FIG. 1A. In FIG. 1B, they are depicted as dotted lines, representing wire (or wire-like) interconnections 250 that have been provided for each of the stimulation electrodes 200 in this example.

The substrate 300 extends along the first transverse axis 700 (considered the width of the stimulation device 100) from a first transverse extent 330 (depicted on the left-hand side) to a second transverse extent 340 (depicted on the right-hand side).

The device 100 may be implanted by first creating a tunnel and/or using an implantation tool.

The return electrode 400 is depicted in FIGS. 1A and 1B, but not in FIG. 1C.

As depicted in FIG. 1B, the stimulation electrode 200 has a longitudinal extent along the longitudinal axis 600 and a transverse extent along the first transverse axis 700. Although depicted as similar, in practice, each stimulation electrode 200 may vary in shape, transverse cross-section, and size (or extent).

FIG. 1C depicts a view of the first surface 310 of the implantable distal end of the device 100, depicted in FIGS. 1A and 1B. In other words, the first surface 310 is depicted in the plane of the paper, lying along the longitudinal axis 600 (depicted from bottom to top) and in the first transverse axis 700 (depicted from right to left). The second transverse axis 750 extends out of the page. The second surface 320 is not depicted in FIG. 1C, but lies at a lower position along the second transverse axis 750 (into the page), and is also substantially parallel to the plane of the drawing.

The one or more interconnections 450 are disposed between the first 310 surface and the second 320 surface, as depicted in FIG. 1A. In FIG. 1C, they are not depicted the one or more interconnections 450 are comprised in an interconnection layer 450 just underneath the first surface 310, with through connections (not depicted) to each of the portions 400*ab* in this example.

It may be convenient to manufacture this first embodiment 100 such that the longitudinal extent 600 of the flexible electrode 400 portions 400*ab* are substantially similar this provides a similar degree of bending flexibility at a plurality of longitudinal 600 dispositions.

After implantation of the device 100, a source of energy may be configured and arranged to provide, in use, electrical energy to the stimulation electrode 200 with respect to the electrical return applied to each portion 400*ab* of the corresponding return electrode 400. As the portions of the return electrode 400 are each directly electrically connected, the electrical return applied is substantially the same for all points along the return electrode portions 400*ab*.

It is advantageous to provide one or more return electrodes 400 proximate the corresponding one or more stimulation electrodes 200 as that may allow a more concentrated electrical field to be used. It may be advantageous to configure and arrange the one or more proximal return electrodes to be disposed within less than 8 mm, preferably less than 6 mm, from the one or more corresponding (active) stimulation electrodes. However, when there is a change in the one or more stimulation electrodes 200 being used for stimulation, it may not be possible to configure an electrode proximate the changed stimulation electrode 200 as an electrical return.

If a plurality of selectable return electrodes 400 are provided, the complexity of the implantable stimulation device may increase, and/or require a more complicated control system. An alternative is to provide a ground electrode 400 with an increased longitudinal 600 and transverse 700 extent, compared to conventional devices however, this may increase the rigidity (increase the bending resistance) of the corresponding section of the substrate due to the metal layer.

Thicker metal layers are generally preferred over thinner metal layers for electrodes 200, 400 because they can be subjected to bodily substances that may dissolve the metal. However, thicker metal layers typically increase rigidity.

An additional design factor is a preference to provide a combined active tissue contact area of the one or more return electrode 400 equal to or more than the active tissue contact area of the one or more active stimulation electrodes 200. The contact areas to be considered are not the total contact surface areas, but the contact areas configured to be active during use and the contact areas that are actually in contact with the surrounding tissue. In general, the ratio between the tissue contact areas does not need to be determined exactly they should be of a similar order of magnitude. For example, it may be sufficient if the combined active tissue contact area of the one or more return electrodes is equal to or more than 70% to 100% of the active tissue contact area of the one or more stimulation electrodes.

By providing one or more bending interruptions 500, the tissue contact area may be optimized due to the enhanced ability of the distal end of a stimulation device to conform to the shape of surrounding tissues and anatomical features. In the example depicted in FIG. 1, one return electrode 400 is provided, and the optimized contact area is up to a maximum of the total contact areas of the two or more electrode portions 400ab.

As depicted in FIG. 1C, the one or more bending interruptions 500 have a transverse 700 extent comparable with the transverse extent of the substrate 300 (in other words, from edge 340 to edge 330). They are disposed substantially along the first transverse axis 700, and are disposed approximately perpendicular to the longitudinal axis 600.

A number of parameters and properties may be considered when configuring and arranging the one or more bending interruptions 500, such as:
  the required curvature orientation in this example, substantially about a plurality of longitudinal 600 dispositions. This may be influenced, for example, by the orientation of the one or more bending interruptions 50 and the separation between the first 400a and second 400b portions.
  the maximum radius of curvature of the substrate 300 at this longitudinal disposition 600. This may be influence, for example, by the separation between the first 400a and second 400b portions, and the bending resistance between the first 400a and second 400b portions.
  The bending resistance between the first 400a and second 400b portions depends on parameters such as:
    the transverse 700 and/or longitudinal extent 600 of the one or more interruptions
    the thickness of the substrate 300, or distance between the first surface 310 and the second surface 320
    the materials comprised in the substrate 300 within the region of the one or more interruptions, and their physical properties. The bending resistance of the substrate 300 material may be increased by including different materials of different thicknesses and different rigidities and/or resilience, such as a reinforcement filament, a metal wire and/or LCP strip.
    the presence of interconnections 250, 450 and/or interconnection layers 450 between the first surface 310 and second surface 320.
    the presence of one or more reinforcement coatings, such as a sputtered layer of chrome.
    the presence of one or more indentations in the first surface 310 and/or second surface 320.
    the presence of one or more electrodes 200, 400 at the longitudinal 600 and/or transverse 700 disposition of the one or more interruptions 500. For example, the stimulation electrodes 200 depicted in FIG. 1A are longitudinally 600 disposed at interruptions between the first 400a and second 400b portions this may increase the bending resistance at these interruptions.

As depicted in FIGS. 1A and 1C, the spacing between the portions 400ab of the flexible return electrode 400 are approximately the same, but the skilled person will realize that each bending interruption may be configured and arranged separately to provide one or more predetermined bending resistances.

One of the insights upon which an aspect of the invention is based is that the inherent flexibility of some substrate materials offers advantages of a high degree of conforming with the shape of surrounding tissue. However, the presence of one or more electrodes 200, 400 may affect the flexibility, resulting in sections of the substrate that are rigid adjacent to more flexible sections. Regions of the electrode surface may be thinned, thickened or removed to provide an optimal bending profile, but this may affect the electrical characteristics of the electrode by affecting the degree to which the different portions of electrode surface area remain substantially contiguous.

Figure 2B:
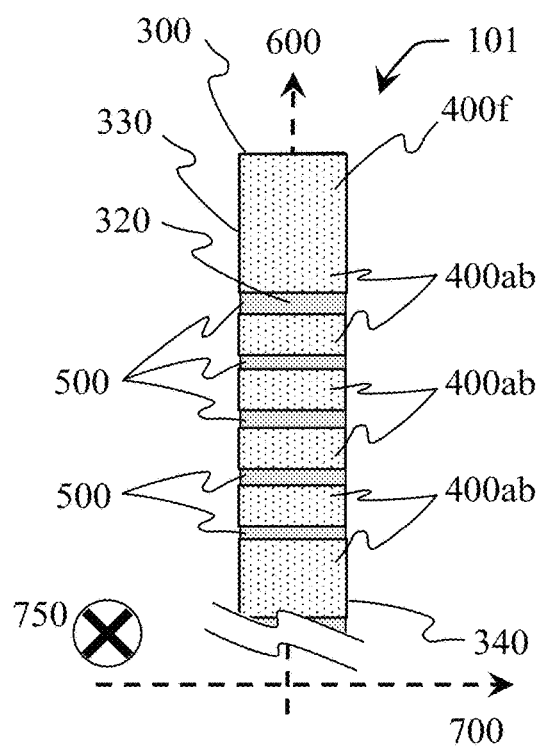
Figure 2C:
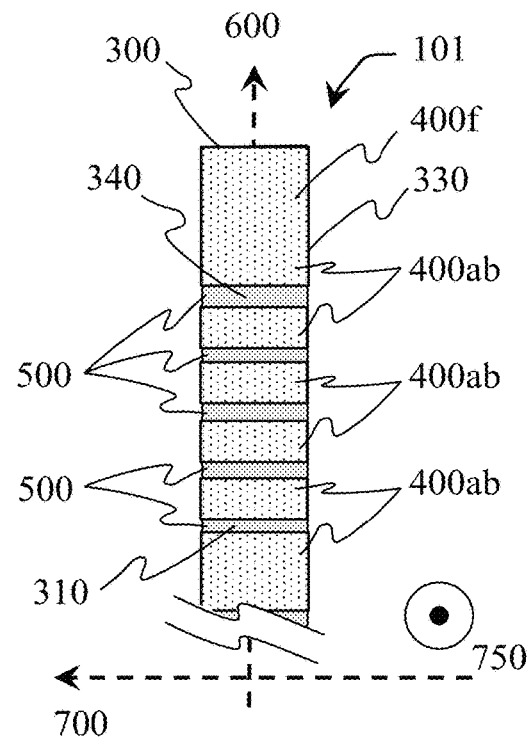

FIGS. 2A, 2B and 2C depict longitudinal cross-sections through a second embodiment 101 of an implantable distal end of a stimulation device comprising. It is similar to the first embodiment 100, depicted in FIG. 1 except:
  instead of one or more separate stimulation electrodes 200, a further flexible electrode 200 is provided, comprised in the second surface 320, and configured, in use, to be in contact with human or animal tissue. This flexible stimulation electrode 200 comprises two or more portions 400a, 400b (400ab), separated by one or more bending interruptions 500.
  the portions 200ab of the flexible stimulation electrode 200 are disposed at substantially the same longitudinal 600 dispositions as the portions 400ab of the flexible return electrode 400. In other words, the bending interruptions 500 of the flexible stimulation electrode 200 are disposed at substantially the same longitudinal 600 dispositions as the bending interruptions 500 of the flexible return electrode 400.
  the one or more interconnections 450 for the return electrode portions 400ab are still an electrical interconnect layer 450. However, they are disposed further away from the first surface 310 (in other words, closer to the second surface 320). In this case, the return electrical interconnect layer 450 includes conductors that connect to each portion 400ab. As before, these conductors are substantially electrically contiguous in use.

the one or more electrical interconnections 250 for the stimulation electrode 200, implemented as wires in FIG. 1, are replaced here by one or more interconnections 250 comprised in a further electrical interconnect layer 250. In this case, they are disposed further away from the second surface 320 (in other words, closer to the first surface 310). In this case, the stimulation electrical interconnect layer 250 includes conductors that connect to each portion 200ab. As before, these conductors are substantially electrically contiguous in use.

By aligning the longitudinal 600 positions of the bending points 500 comprised in the first 310 and second 320 surfaces, a very flexible substrate is provided 300, with a high uniformity of bending resistance as the interruptions are configured and arranged substantially the same.

Alternatively, the flexible stimulation electrode 200 may also be comprised in the first surface 310. The device may comprise a plurality of flexible stimulation electrodes 200 comprised in the first 310 and/or second 320 surface.

Although the electrodes comprised in the top surface 310 are indicated as one or more return electrodes 400, and the electrodes comprised in the bottom surface 320 are indicated as stimulation electrodes 200, the skilled person will realize that the functionalities of the electrodes 200, 400 may be modified by changing the electrics connections to the distal end. This may be advantageous if it is uncertain whether the implantable distal end is above or below the targeted tissue for example, above or below a nerve.

Figure 3A:
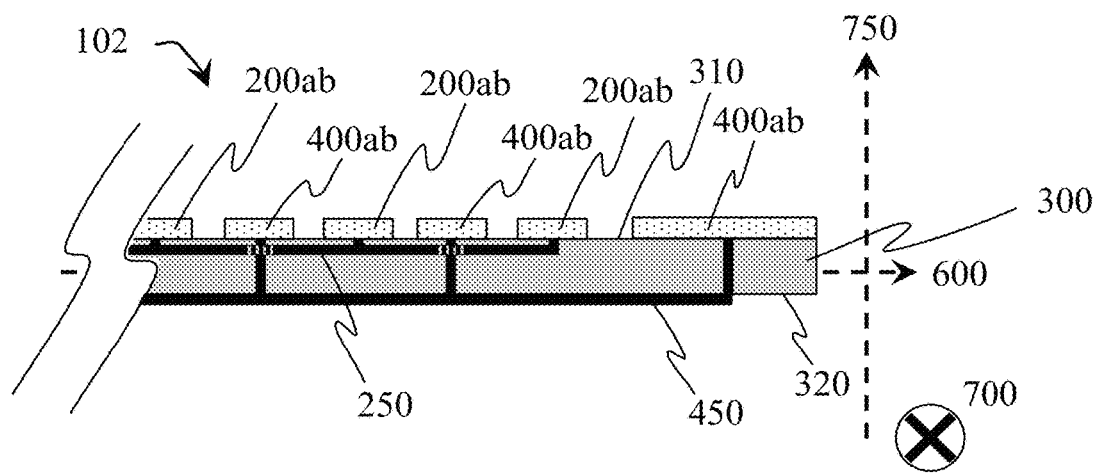
FIGS. 3A, 3B and 3C depicts a third example of an implantable distal end of a stimulation device.
Figure 3B:
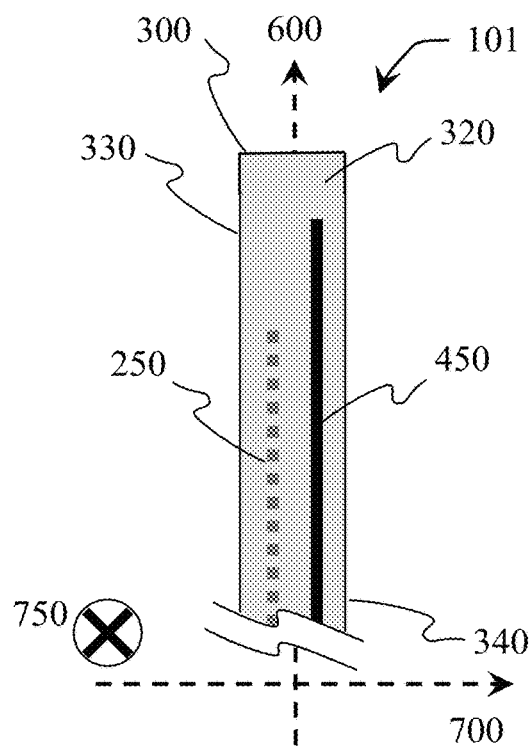
Figure 3C:
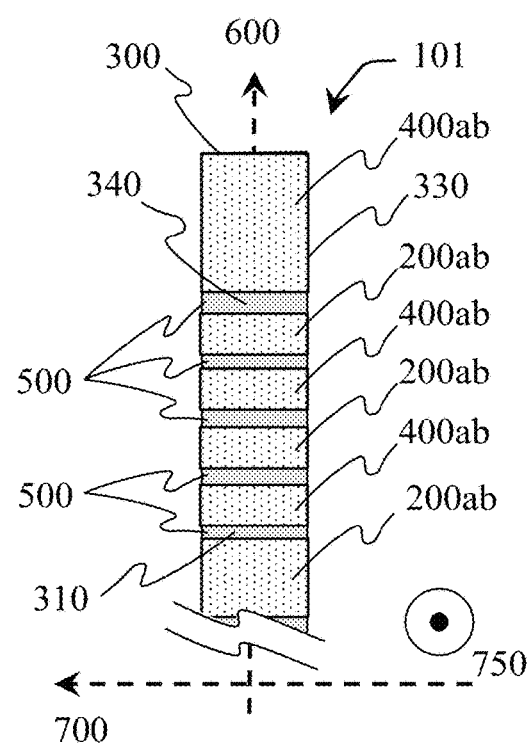

FIGS. 3A, 3B and 3C depict longitudinal cross-sections through a third embodiment 102 of an implantable distal end of a stimulation device. It similar to the second embodiment 101 depicted in FIG. 2 except:

- instead of a flexible stimulation electrode 200 comprised in the second surface 320, a flexible stimulation electrode 200 is comprised in the first surface 310. No electrodes are comprised in the second surface 320.
- the portions 400ab of the flexible return electrode 400 and the portions 200ab of the flexible stimulation electrode 200 are comprised in the first surface 310 and alternated (interposed).
- the one or more interconnections 450 for the return electrode portions 400ab are implemented in this example as a wire or wire-like (depicted in FIG. 3B as a dashed line). In this case, the interconnections 450 are comprised in the second surface 320 and include conductors that connect to each portion 400ab passing through almost the whole thickness of the substrate 300. In this case, the one or more return interconnections 450 context of this disclosure are not configured or arranged to be, in use, in contact with human or animal tissue. For example, they are rendered low conductance and/or insulating by including one or more layers (not depicted) between the interconnection 450 and any human or animal tissue.
- the one or more interconnections 250 for the stimulation electrode portions 200ab are implemented in this case as a wire or wire-like (depicted in FIG. 3B). In this case, the interconnections 450 are comprised between the first surface 310 and the second surface 320, include conductors that connect to each portion 400ab passing through almost the whole thickness of the substrate 300.

The advantage of this embodiment may be increased local field strengths due to the low degree of separation between the stimulation 200ab electrode portions and the return 400ab portions.

Alternatively, the flexible stimulation electrode 200 and return flexible electrode 400 may be comprised in the second surface 320. The device may comprise a plurality of flexible stimulation electrodes 200 comprised in the first 310 and/or second 320 surface.

For clarity, no contiguous portions 470 are depicted, but the bending points 500 may be of any configuration described above in relation to FIG. 4A and FIG. 4B.

Figure 4A:
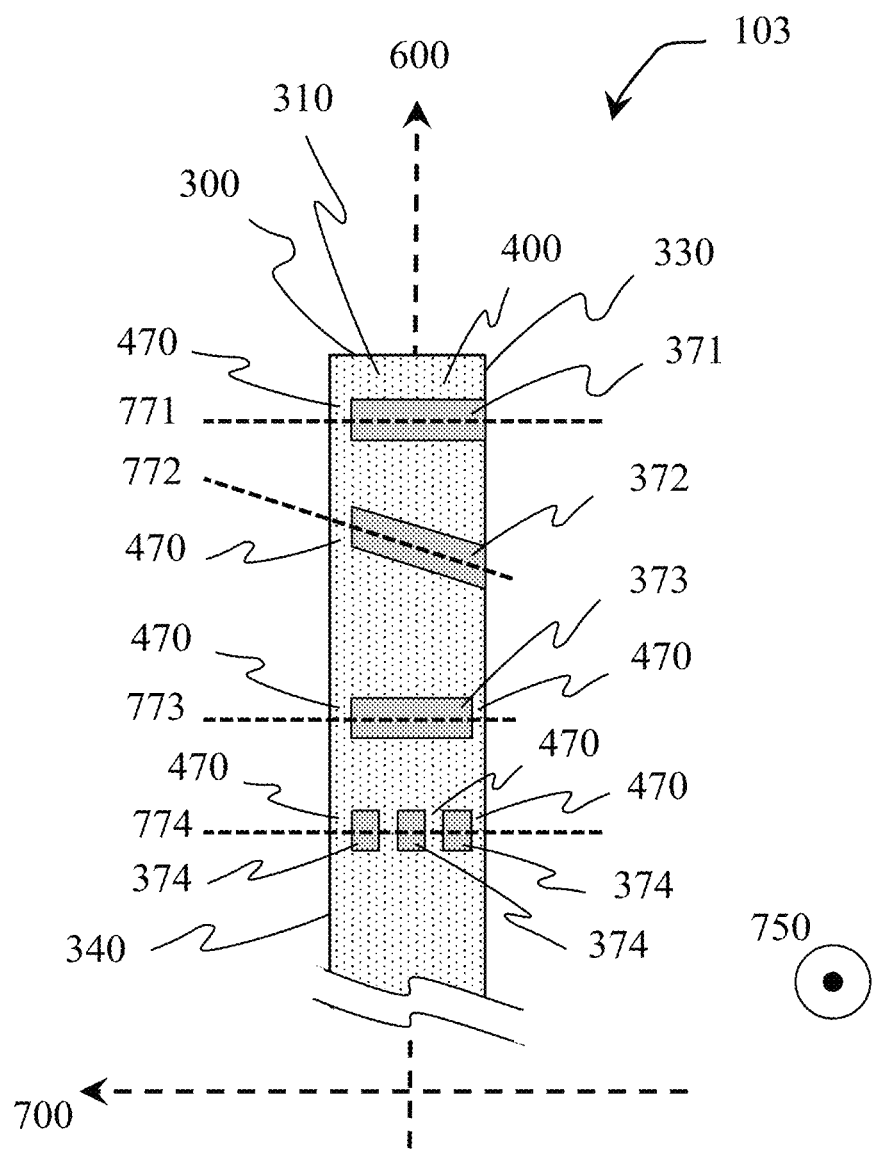
FIGS. 4A and 4B depicts a fourth and fifth example of an implantable distal end of a stimulation device.
Figure 4B:
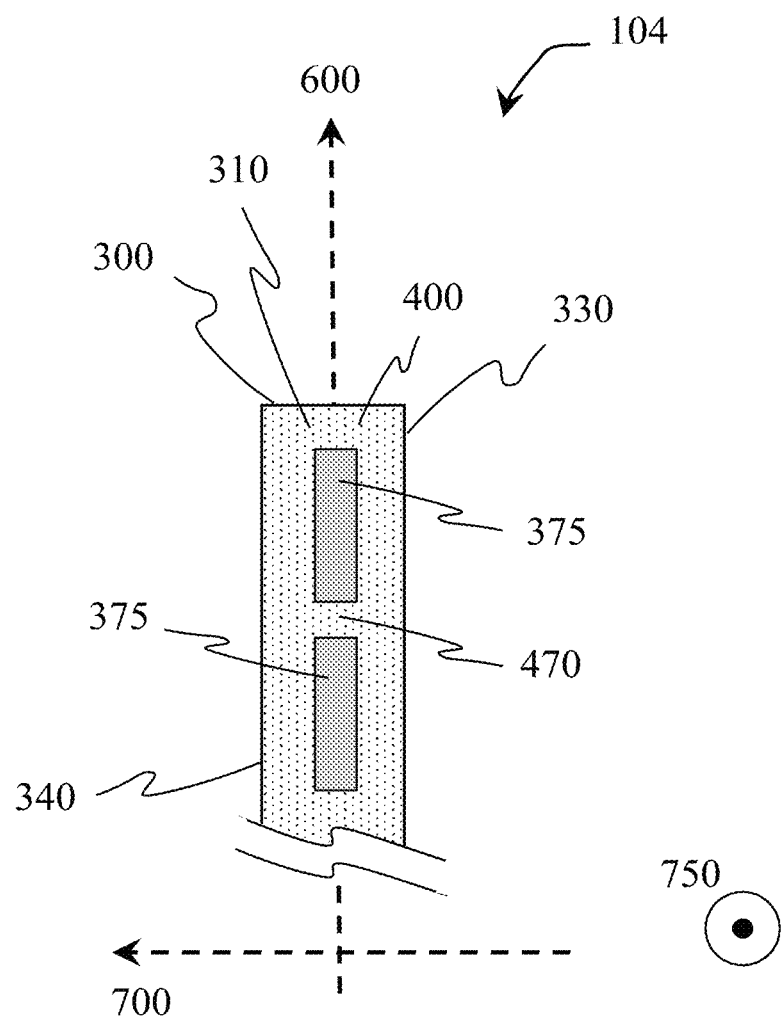

FIGS. 4A and 4B depict a fourth 103 and fifth 104 example of an implantable distal end of a stimulation device in both cases a view of the first surface 310 of the implantable distal end of these devices. They are modifications of the return electrode 400 depicted in FIG. 1C or FIG. 2C. FIGS. 4A and 4B also depict a flexible electrode 400 with a longitudinal extent along the longitudinal axis 600, and a transverse extent along the first transverse axis 700, the transverse axis 700 being substantially perpendicular to the longitudinal axis 600. The flexible electrode 400 comprises, in general, one or more bending interruption 500.

FIG. 4A depicts a flexible return electrode 400 comprising a plurality of pairs of portions, separated by four differently configured specific bending interruptions 371, 372, 373, 374. Three of them 371, 373, 374 provide bending around approximately transverse bending axes 771, 773, 774. One of the bending interruptions 372 provides bending around a bending axis 772 at an angle to the first transverse axis 700 in other words, it allows diagonally-oriented bending.

FIG. 4B depicts a flexible return electrode 400 comprising a one pair of portions, separated by bending interruptions 375, configured and arranged to allow bending around approximately the substrate longitudinal axis 600.

Each bending point in FIGS. 4A and 4B comprise one or more bending interruptions, 371, 372, 373, 374, 375 configured and arranged to allow an orientation of each corresponding first portion plane to deviate from an orientation of each corresponding second portion plane at the one or more bending interruptions 371, 372, 373, 374, 375 in other words, they allow bending around the corresponding bending axes 771, 772, 773, 774, 600. However, in these cases, each of the bending interruptions, 371, 372, 373, 374, 375 provides a different possible deviation and/or bending resistance.

FIG. 4A depicts a first bending interruption 371, approximately disposed along the first transverse axis 700. It is disposed along a first bending axis 771 to provide a first bending point 771—the interruption 371 is an area of increased flexibility compared to the immediately proximate portions of the electrode 400. This may be achieved by providing a region with a variation in a relevant parameter such as those indicated above—for example, a region of substantially thinner electrode, a region of no electrode material (an opening) and/or a region comprising a different electrode material and/or coating. As the first bending interruption 371 is disposed approximately along the first transverse axis 700, the first bending interruption 371 is configured and arranged to allow the plane of a first portion of the first 310 surface between the first bending interruption 371 and the distal end (more positive along the longitudinal axis 600) to deviate from the plane of a second portion of the first 310 surface between the first bending interruption 371 and the proximal end (more negative along the longitudinal axis 600). By suitable configuration, the substrate 300 may allow bending away from the first surface 310 and/or away from the second surface 320.

Optionally, the first bending interruption 371 may comprise one or more openings—in other words, the flexible electrode 400 is no longer contiguous at this point and bending is mainly determined by the properties of the substrate. Openings may be advantageous because they are relatively straightforward to create, and they also may provide a visual clue to a healthcare professional who is implanting the substrate section where the bending axes are disposed.

Additionally, it may be advantageous to provide a further connection between adjacent portions separated by the one or more interruptions 371 this further connection comprises one or more contiguous portions proximate the one or more bending interruptions 371—here one contiguous portion 470 is depicted between a transverse edge of the interruption 371 and the edge 340 of the substrate 300.

As in the configurations described above, the electrical connection between the portions is provided through the one or more interconnections 450, disposed between the first 310 and second 320 surfaces.

The contiguous portion 470 forms part of the electrode conductive layer, and may therefore be considered as an additional electrical connection. But, this contiguous portion 470 therefore may be substantially configured to increase or to maintain the bending resistance at the bending axes, and any effect on the conductivity (for example, due to making the contiguous portion 470 thinner and/or narrower) does not substantially affect the operation of the flexible electrode 400.

One of the insights upon which an aspect of the invention is based is that the shape of the conductive electrode material may be configured and arranged to maintain or to increase the bending resistance at a bending axis. One or more regions of the electrode proximate a bending interruption may be thinned, thickened or shaped to provide a predetermined bending resistance using a region of the electrode that remains contiguous. The presence of interconnections allows a very high degree of bending resistance configurability without affecting the electrical characteristics of the flexible electrode 200, 400.

The one or more bending interruptions 371 and/or one or more openings may be formed using any suitable material removal (or partial removal) techniques, such as lithography, chemical etching, using a laser, using a mechanical scribe and any combination thereof. It is therefore straightforward to provide relatively complex shapes.

Additionally or alternatively, a similar configuration and arrangement may be achieved by increasing the amount of material present proximate the first bending interruption 371, using, for example, coatings and/or ridges made of substrate material 300.

The skilled person will realize that the degree of bending, the direction of the bending and the disposition may be provided by a suitable arrangement and configuration of the one or more bending interruptions 371 and a suitable arrangement and configuration of the optional one or more openings. For example, the skilled person may predetermine the degree of bending by configuring the length (longitudinal extent 600), the width (transverse extent 700) and the shape. The shape may include, for example, such geometries as rectangle, square, trapezium, polygon.

FIG. 4A further depicts a second bending interruption 372, disposed at approximately 20 degrees to the first transverse axis 700. It is similar to the first bending interruption 371, except:
  the second bending interruption 372 is disposed along a second bending axis 772, which is at an angle of approximately 20 degrees to the first transverse axis 700 and approximately 70 degrees to the longitudinal axis 600.
Similarly, a proximate contiguous portion 470 is provided to increase or maintain bending resistance.

Any angle may be used to provide a corresponding angle of bending axis/point 772.

FIG. 4A further depicts a third bending interruption 373, disposed along a third bending axis 773 which is approximately also along the first transverse axis 700. It is similar to the first bending interruption 372, except for:
  an additional contiguous portion 470 is provided between an edge 330 of the substrate 300 and the transverse edge of the interruption 373.
Both contiguous portions 470 may be configured and arranged to increase or maintain bending resistance.

FIG. 4A further depicts a fourth bending point comprising three interruptions 374, disposed along a fourth bending axis 774, which is approximately also along the first transverse axis 700. It is similar to the third bending interruption 373, except for:
  comprising three bending interruptions 374, each one having less than one-third of the transverse extent of the third bending interruption 373,
  comprising four contiguous portions 470.
Both contiguous portions 470 may be configured and arranged to increase or maintain bending resistance.

FIG. 4B depicts a fifth example 104 of an implantable distal end of a stimulation device.

The fifth example 104 comprises a fifth bending point comprising two interruptions 375, approximately disposed approximately along a longitudinal axis 600. The interruptions 375 are similar to the bending interruptions described above in relation to FIG. 4A.

In this case, a contiguous portion 470 is provided proximate and between the two bending interruptions 375, disposed approximately along the longitudinal axis 600.

The contiguous portion 470 may be configured and arranged to increase or maintain bending resistance.

The skilled person will realize that any number of interruptions may be provided, as well as any number of contiguous portions, to provide the desired bending resistance, the desired degree of flexibility, and at the desired angle. This allows the substrate 300 to conform to neighboring anatomical tissue if made flexible enough, with a low degree of bending resistance, the substrate 300 may conform by being pressed against neighboring tissue at the point of implantation. Additionally or alternatively, the flexibility may be slightly less, allowing a health professional to bend the substrate to the appropriate conformation shape before and/or during implantation.

In addition, a plurality of interruptions may be provided at different angles, allowing different shapes of the electrode portions. For example, one or more electrode portions 200*ab*, 400*ab*, separated by one or more interruptions may be provided to provide a substrate 300 that bends in two or more directions. The electrode portions may be, for example, polygonal, rectangular, square, trapezoidal in shape.

Alternatively or additionally, such bending interruption 371, 372, 373, 374, 375 may be comprised in a flexible stimulation electrode 200 comprised in the first surface 310. Alternatively or additionally, one or more bending interruptions 371, 372, 373, 374, 375 may be comprised in a flexible electrode 200, 400 comprised in the second surface 320.

Figure 9:
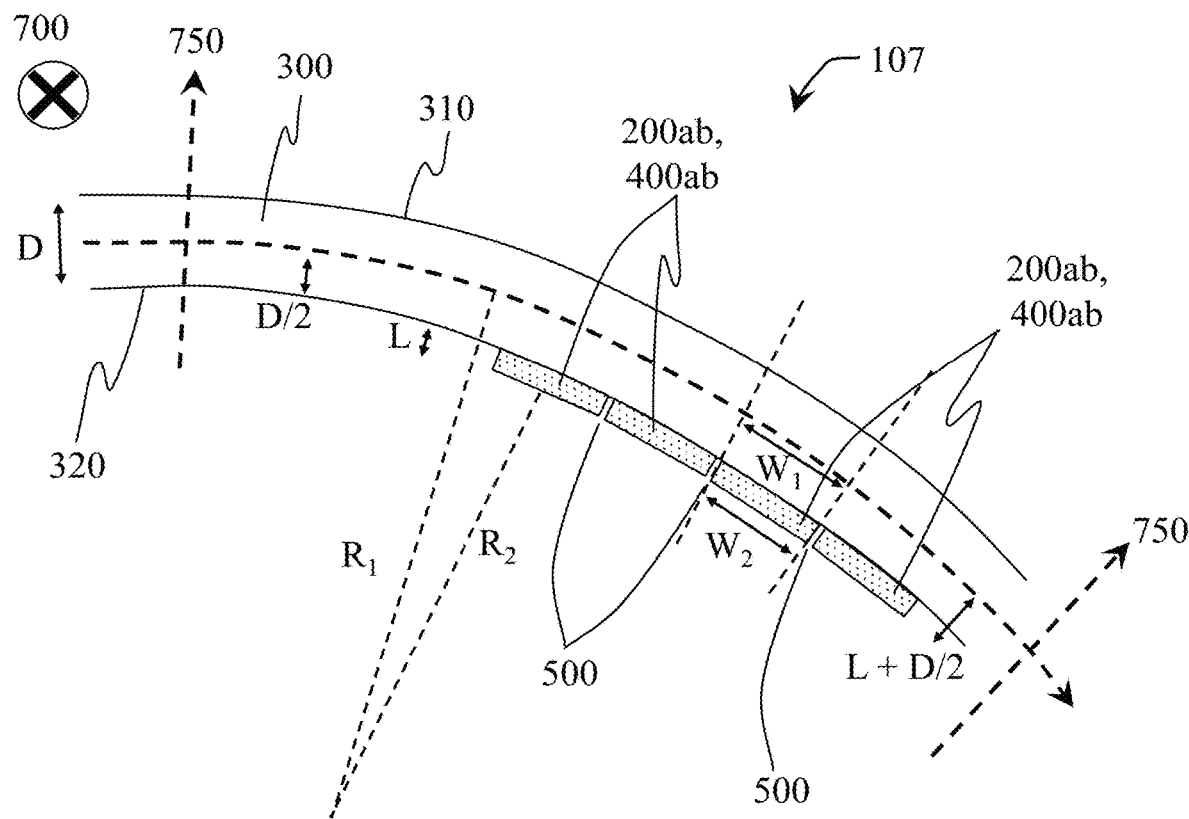
FIG. 9 depicts an example of configuring and arranging a device to be conformable to a predetermined curvature.

FIG. 9 depicts an example of configuring and arranging a device to be conformable to a predetermined curvature. A substrate 300 is depicted in longitudinal cross-section, elongated along a longitudinal axis 600. The longitudinal axis 600 is depicted with the desired curvature. The substrate 300 has a first 310 and second 320 surface disposed along substantially parallel curved transverse planes 600, 700.

As depicted, the first surface 310 lies in a plane comprising the longitudinal axis 600 and a first transverse axis 700—the first transverse axis 700 is substantially perpendicular to the longitudinal axis 600. As depicted, the curved plane of the first surface 310 and second surface 320 are substantially perpendicular to the plane of the cross-section drawing (substantially perpendicular to the surface of the paper). The substrate 300 has a thickness or extent along a second transverse axis 750 of D this second transverse axis 750 is substantially perpendicular to both the longitudinal axis 600 and the first transverse axis 700 it lies in the plane of the drawing (along the surface of the paper) as depicted.

A flexible electrode 200, 400 is provided, separated into four portions 200*ab*, 400*ab*, comprised in the curved second surface 320. This may be any of the stimulation electrodes and/or return electrodes described above. The electrode 200, 400 comprises three bending interruptions 500, providing three bending points/axis (not depicted) approximately along the first transverse axis 700. For clarity, no contiguous portions 470 are depicted, but the bending points 500 may be of any configuration described above in relation to FIG. 4A and FIG. 4B.

As depicted, the nominal curvature of the substrate 300 is R1—from the center point of the curvature to the central plane which is midway between the first 310 and second 320 surface along the second transverse axis 750. The conformed curvature of the substrate 300 is R2—from the center point of the curvature to the curved second surface 320. The thickness of the electrodes (extent along the second transverse axis 750) is labelled as L. The thickness of the substrate 300 (extent along the second transverse axis 750) is labelled as D. W2 is the pitch between portions. W1 is the longitudinal extent 600 of the electrode portion.

Typical values are:
R1: 100 mm
D/L: 0.150 mm
L: 0.050 mm
Calculation is as follows with typical values:

$$R2 = R1 - (D/2 + L)$$

$$W2/W1 = 2\pi R2 / 2\pi R1 = R2/R1$$

$$R2/R1 = (R1 - (D/2 + L))/R1 = 1 - (D/2 + L)/R1$$

With these typical values, W2/W1=0.998 or 99.8%

So, by providing bending interruptions 500 with an extent along the longitudinal axis of 1.2% compared to the electrode portion 200*ab*, 400*ab*, and the substrate 300 comprises a sufficiently flexible substrate, then the device may be bent to conform with a radius of curvature of 100 mm or less. A smaller radius of curvature means a higher degree of bending.

Typically, curvatures that the implantable distal end of a stimulation device must conform to may be determined by measurement of patients.

Additionally or alternatively, databases such as the DINED database (from 2004) of body measurements may be used to determine typical values. Dimensions of these 3D human models are based on anthropometric data from a survey done in the Netherlands in 2004. P50 refers to the percentile of people participating in the study:

for a frontal implant, male P50 curvatures from 2004 are horizontal radius 75.124 mm, vertical radius 96.615 mm;

for a frontal implant, female P50 curvatures from 2004 are horizontal radius 71.089 mm, vertical radius 93.108 mm;

for an occital implant, male P50 curvatures from 2004 are horizontal radius 74.916 mm, vertical radius 96.095 mm;

for an occital implant, female P50 curvatures from 2004 are horizontal radius 70.641 mm, vertical radius 91.42 mm;

So, by suitable configuration, a radius of curvature of 90 mm to 96 mm may be provided.

Dimensions of these 3D human models are based on anthropometric data from a survey done in the Netherlands in 2004. P50 refers to the percentile of people participating in the study. For both the frontal and occipital area, the radius of the most curved edges is defined by means of an osculating circle:

for male P50, the radius frontal osculating circle 63.019 mm;

for male P50, the radius occipital osculating circle 60.458 mm;

for female P50, the radius frontal osculating circle 58.195 mm;

for female P50, the radius occipital osculating circle 56.228 mm;

So, by suitable configuration, a radius of curvature of 55 mm to 65 mm may be provided.

Dimensions of these 3D human models are based on anthropometric data from a survey done in the Netherlands in 2004. P5 and P95 refers to the percentile of people participating in the study, with P5 representing the smallest person and P95 the largest person of the total sample.

For both the frontal and occipital area, the radius of the most curved edge is defined by means of an osculating circle:

for male P95, the horizontal radius 79.00 mm, the vertical radius 100.477 mm and the radius frontal osculating circle 67.361 mm;

for male P95, the horizontal radius 79.423 mm, the vertical radius 102.003 mm, the radius occipital osculating circle 66.237 mm;

for female P5, the horizontal radius 64.68 mm, the vertical radius 83.336 mm and the radius frontal osculating circle 49.585 mm; and for female P5, the horizontal radius 65.578 mm, the vertical radius 85.21 mm and the radius occipital osculating circle 48.035 mm So, by suitable configuration, a radius of curvature of 45 mm to 80 mm may be provided.

Figure 8:
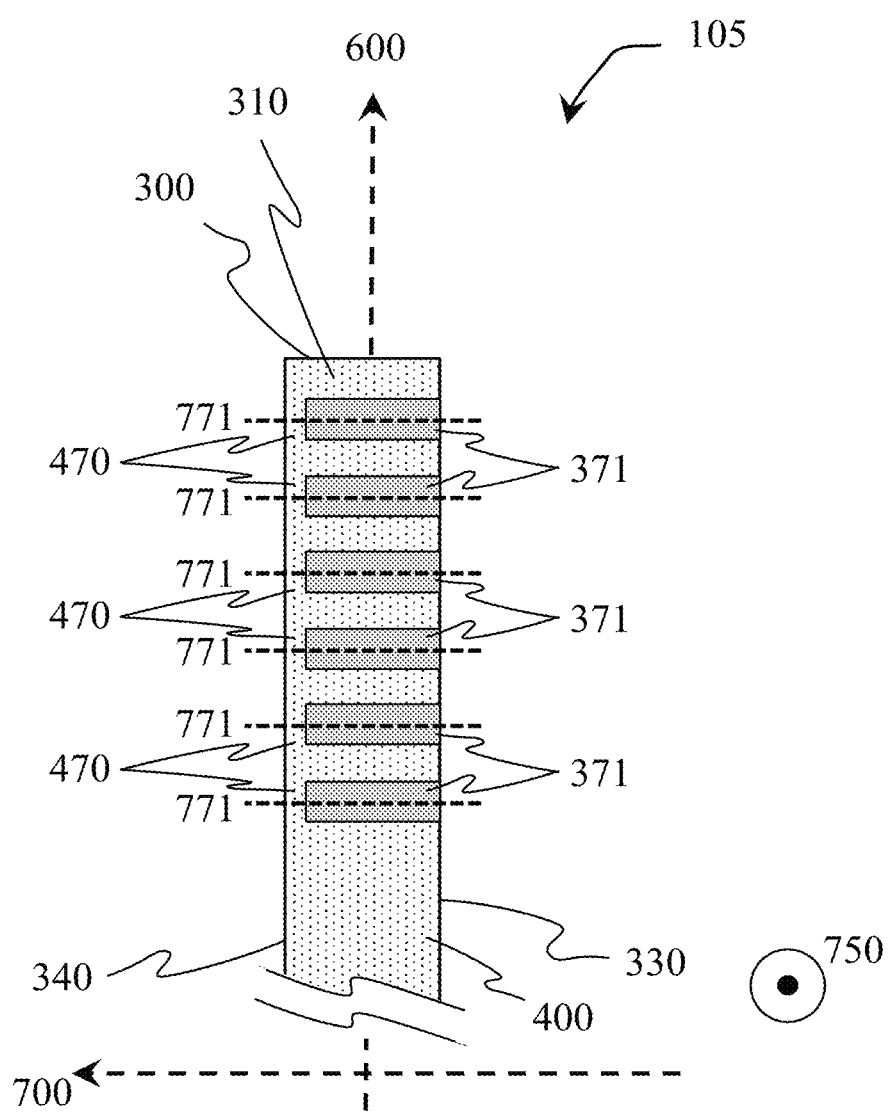
FIG. 8 depicts a view of the first surface of an implantable distal end of a stimulation device.

FIG. 8 depicts a view of the first surface 310 of a sixth 105 example of an implantable distal end of a stimulation device.

It is a modification of the flexible return electrode 400 depicted in FIG. 4A. It also depicts a flexible electrode 400 with a longitudinal extent along the longitudinal axis 600, and a transverse extent along the first transverse axis 700, the transverse axis 700 being substantially perpendicular to the longitudinal axis 600. The flexible electrode 400 comprises, in general, one or more bending interruption 500.

FIG. 8 differs from FIG. 4A:
it comprises a plurality of electrode portions 400*ab*, separated by six bending interruptions 371 (as depicted in FIG. 4A), configured and arranged to provide substantially the same bending properties and substantially the same bending resistance between each of the portions 400*ab*, around a plurality of bending axes 771. In this case, the bending axis 771 is approximately the same as the first transverse axis 700. A high uniformity of bending resistance is provided due to the interruptions 771 being configured and arranged to be substantially the same.

Figure 5:
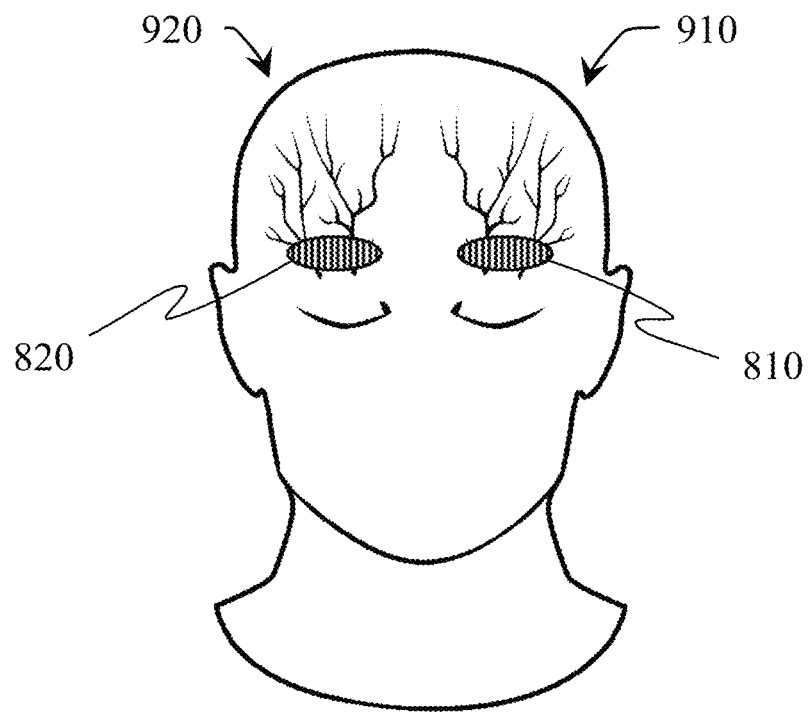
FIG. 5 and FIG. 6 depict examples of nerves that may be stimulated to treat headaches.
Figure 6:
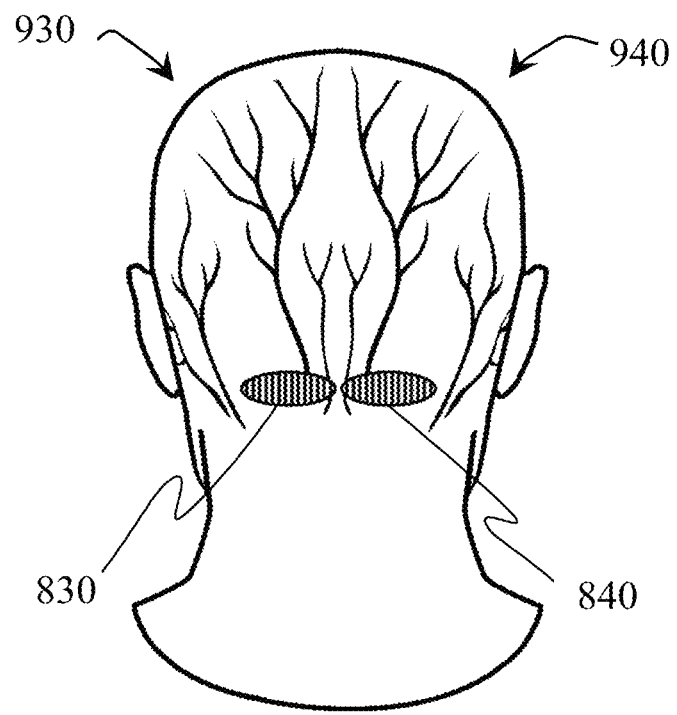

FIG. 5 and FIG. 6 depict examples of nerves that may be stimulated using a suitably configured implantable distal end of stimulation devices 100, 101, 102, 103, 104, 105, 106, 107 to provide neuro stimulation to treat, for example, headaches or primary headaches.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the distal part of the stimulation device comprising stimulation devices 100, 101, 102, 103, 104, 105, 106, 107 are depicted as regions:

location 810 for left supraorbital stimulation and location 820 for right supraorbital stimulation for treating chronic headache such as migraine and cluster.

location 830 for left occipital stimulation and location 840 for right occipital stimulation for treating chronic headache such as migraine, cluster, and occipital neuralgia.

In many cases, these will be the approximate locations 810, 820, 830, 840 for the implantable device 100, 101, 102, 103, 104, 105, 106, 107.

For each implant location, 810, 820, 830, 840 a separate stimulation system may be used. Where implant locations 810, 820, 830, 840 are close together, or even overlapping, a single stimulation system may be configured to stimulate at more than one implant location 810, 820, 830, 840.

A plurality of stimulation devices 100, 101, 102, 103, 104, 105, 106, 107 may be operated separately, simultaneously, sequentially or any combination thereof to provide the required treatment.

Figure 7:
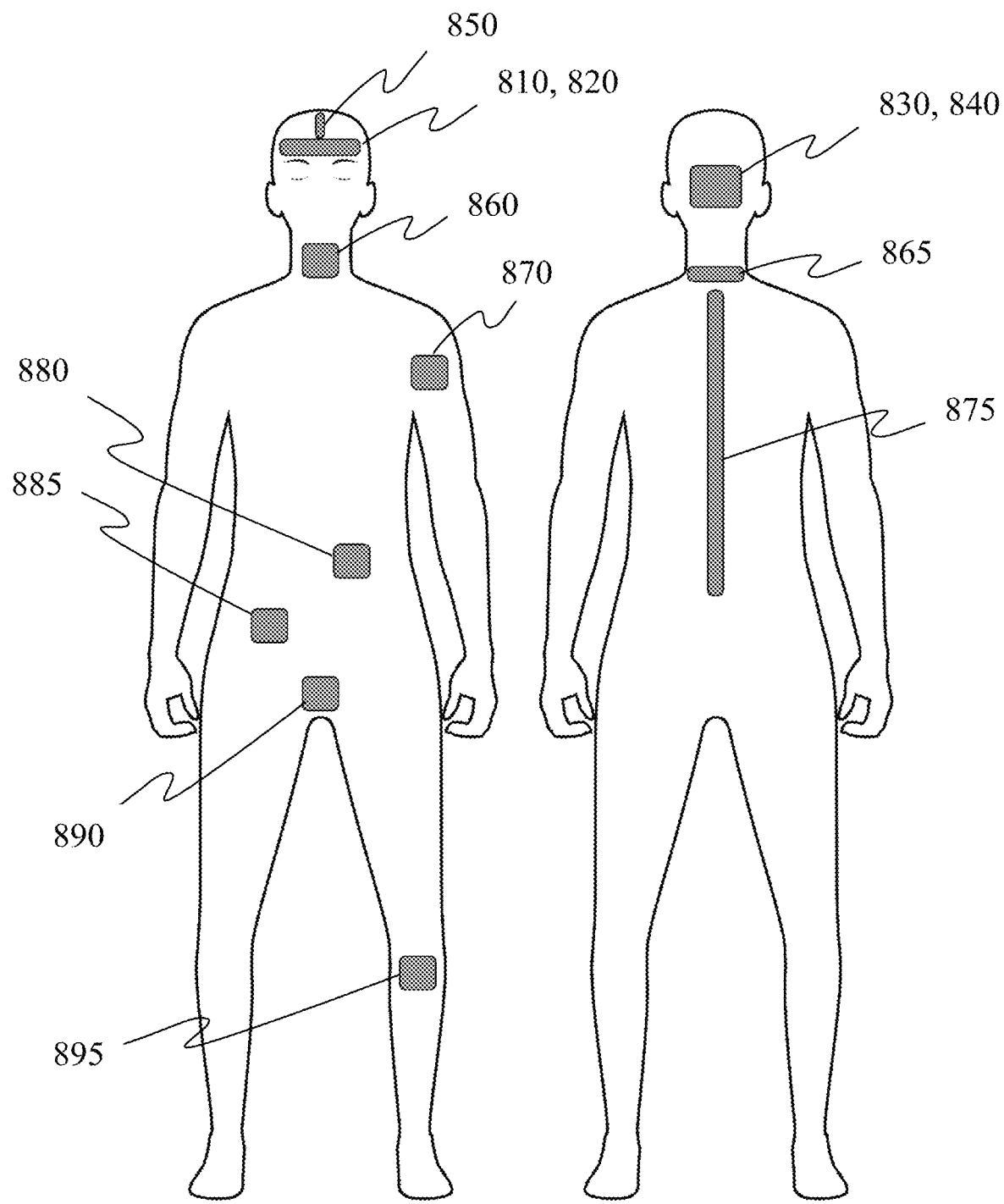
FIG. 7 depicts examples of nerves that may be stimulated for other treatments.

FIG. 7 depict further examples of nerves that may be stimulated using a suitably configured improved implantable device 100, 101, 102, 103, 104, 105, 106, 107 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

location 810 for cortical stimulation for treating epilepsy;
location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery;
location 860 for vagus nerve stimulation for treating epilepsy, depression, anxiety, bulimia, obesity, tinnitus, obsessive compulsive disorder and heart failure;
location 860 for carotid artery or carotid sinus stimulation for treating hypertension;
location 860 for hypoglossal & phrenic nerve stimulation for treating sleep apnea;
location 865 for cerebral spinal cord stimulation for treating chronic neck pain;
location 870 for peripheral nerve stimulation for treating limb pain, migraines, extremity pain;
location 875 for spinal cord stimulation for treating chronic lower back pain, angina, asthma, pain in general;
location 880 for gastric stimulation for treatment of obesity, bulimia, interstitial cystitis;
location 885 for sacral & pudendal nerve stimulation for treatment of interstitial cystitis;
location 885 for sacral nerve stimulation for treatment of urinary incontinence, fecal incontinence;
location 890 for sacral neuromodulation for bladder control treatment; and
location 895 for fibular nerve stimulation for treating gait or footdrop.

Other condition that may be treated include gastroesophageal reflux disease and inflammatory diseases.

The descriptions thereof herein should not be understood to prescribe a fixed order of performing the method steps described therein. Rather the method steps may be performed in any order that is practicable. Similarly, the examples are used to explain the algorithm, and are not intended to represent the only implementations of these algorithms the person skilled in the art will be able to conceive many different ways to achieve the same functionality as provided by the embodiments described herein.

Many types of implantable distal ends of stimulation devices are depicted. But this does not exclude that the rest of the device is implanted. This should be interpreted as meaning that at least the electrode section of the distal end is preferably configured and arranged to be implanted.

In general, for any of the configurations described and depicted in this disclosure, any electrode 200, 400 may be connected as either a stimulating 200 or return electrode 400. This may be advantageous if it is uncertain whether the implantable distal end is above or below the targeted tissue for example, above or below a nerve.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

REFERENCE NUMBERS USED IN DRAWINGS

100 a first implantable distal end of a stimulation device
101 a second implantable distal end of a stimulation device
102 a third implantable distal end of a stimulation device
103 a fourth implantable distal end of a stimulation device
104 a fifth implantable distal end of a stimulation device
105 a sixth implantable distal end of a stimulation device
106 a first implantable distal end of a stimulation device
200 one or more stimulation electrodes 200ab one or more stimulation electrode portions
250 one or more stimulation electrical interconnections
300 an elongated substrate
310 a first substantially planar transverse surface
320 a second substantially planar transverse surface
371 a first bending interruption
372 a second bending interruption
373 a third bending interruption
374 a fourth bending interruption
375 a fifth bending interruption
400 one or more return electrodes
400ab one or more return electrode portions
450 one or more return electrical interconnections
470 one or more contiguous portions
500 a bending interruption
600 a longitudinal axis
700 a first transverse axis
750 a second transverse axis
771 a first bending axis/point
772 a second bending axis/point
773 a third bending axis/point
774 a fourth bending axis/point
810 location for left supraorbital nerve or cortical stimulation
820 location for right supraorbital stimulation
830 location for left occipital nerve stimulation
840 location for right occipital nerve stimulation
850 location for deep brain stimulation
860 location for vagus nerve, carotid artery, carotid sinus, phrenic nerve or hypoglossal stimulation
865 location for cerebral spinal cord stimulation
870 location for peripheral nerve stimulation
875 location for spinal cord stimulation
880 location for gastric stimulation
885 location for sacral & pudendal nerve stimulation
890 location for sacral neuromodulation
895 location for fibular nerve stimulation
910 left supraorbital nerve
920 right supraorbital nerve
930 left greater occipital nerve
940 right greater occipital nerve

The invention claimed is:

1. An implantable stimulation device comprising:
an elongated substrate disposed along a longitudinal axis, the substrate having a first and second surface, the substrate further comprising:
a flexible electrode; and
one or more interconnections disposed between the first and second surface;
the flexible electrode further comprising:
a first portion, disposed along a first portion plane, and
a second portion, disposed along a second portion plane, the first portion and second portion being in direct electrical connection through the one or more interconnections while being physically separated by one or more bending interruptions;
wherein the one or more bending interruptions are configured and arranged to have a lower bending resistance than the first and second portion whereby an orientation of the first portion plane is allowed to deviate from an orientation of the second portion plane at the one or more bending interruptions.

2. The implantable stimulation device according to claim 1, wherein:
a conformable shape of the flexible electrode in cross-section comprises the one or more bending interruptions separating two portions having a higher rigidity than the one or more bending interruptions.

3. The implantable stimulation device according to claim 1, wherein:
the flexible electrode has a longitudinal extent along the longitudinal axis; and
the one or more bending interruptions are configured and arranged to allow a deviation around the longitudinal axis.

4. The implantable stimulation device according to claim 1, wherein:
the flexible electrode has a transverse extent along a first transverse axis, the first transverse axis being substantially perpendicular to the longitudinal axis; and
the one or more bending interruptions are configured and arranged to allow a deviation around the first transverse axis.

5. The implantable stimulation device according to claim 1, wherein:
a tissue contact surface of the first portion is disposed along the first portion plane, and
a tissue contact surface of the second portion is disposed along the second portion plane.

6. The implantable stimulation device according to claim 1, wherein the flexible electrode further comprises one or more contiguous portions proximate the one or more bending interruptions, configured and arranged to increase or to maintain a bending resistance between the first and second portions.

7. The implantable stimulation device according to claim 1, wherein the one or more bending interruptions comprise one or more openings.

8. The implantable stimulation device according to claim 1, wherein:
the flexible electrode is configured and arranged as a stimulation electrode, configured and arranged to provide stimulation energy to human or animal tissue.

9. The implantable stimulation device according to claim 1, wherein:
the flexible electrode is configured and arranged as a return electrode.

10. The implantable stimulation device according to claim 9, wherein the device further comprises one or more stimulation electrodes, and the return electrode is configured to provide, in use, an electrical return for the one or more stimulation electrodes.

11. The implantable stimulation device according to claim 10, wherein the one or more stimulation electrodes are comprised in the second surface, and the return electrode is comprised in the second surface.

12. The implantable stimulation device according to claim 10, wherein the one or more stimulation electrodes and the return electrode are comprised in the first or second surface.

13. The implantable stimulation device according to claim 1, wherein the substrate further comprises one or more further interconnections, disposed between the first and second surface; the one or more further interconnections being configured and arranged to provide the flexible electrode with stimulation energy.

14. The implantable stimulation device according to claim 1, wherein the substrate comprises a material selected from the group consisting of:
a Liquid Crystal Polymer LCP, a Polyimide, parylene, a biocompatible polymer, a biocompatible elastomer, and combinations thereof.

15. A stimulation system comprising:
an implantable stimulation device according to claim 1; and
a source of electrical energy, configured and arranged to provide, in use, energy to the flexible electrode.

16. A method of stimulation, comprising:
stimulating, by the stimulation system of claim 15, a body part selected from the group consisting of: one or more nerves, one or more muscles, one or more organs, spinal cord tissue, and combinations thereof.

17. A method of treatment, comprising:
treating, by the stimulation system of claim 15, a condition selected from the group consisting of: headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, poststroke pain, obesity, and combinations thereof.

18. A method of stimulation, comprising:
stimulating, by the implantable stimulation device according to claim 1, a body part selected from the group consisting of: one or more nerves, one or more muscles, one or more organs, spinal cord tissue, and combinations thereof.

19. A method of treatment, comprising:
treating, by the implantable stimulation device according to claim 1, a condition selected from the group consisting of: headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, poststroke pain, obesity, and combinations thereof.

20. The implantable stimulation device according to claim 1, wherein the direct electrical connection is such that stimulation voltage is substantially identical in the first and second portions at substantially a same time.

21. The implantable stimulation device according to claim 1, wherein the first and second portions have a same electrical connection to an electrical energy source.

22. An implantable stimulation device comprising:
an elongated substrate having a first surface and a second surface, the elongated substrate comprising:
a flexible electrode comprising a first electrode portion and a second electrode portion, and
one or more electrical interconnections disposed between the first surface and the second surface,
wherein the first electrode portion and the second electrode portion are physically separated by one or more bending interruptions while being in direct electrical connection with each other through the one or more electrical interconnections,
wherein the flexible electrode is configured to deform by bending at the one or more bending interruptions, and
wherein the elongated substrate is disposed along a longitudinal axis.

* * * * *